(12) United States Patent
Taka et al.

(10) Patent No.: US 7,396,858 B2
(45) Date of Patent: Jul. 8, 2008

(54) BIGUANIDE DERIVATIVE AND THERAPEUTIC AGENT FOR DIABETES CONTAINING THE SAME

(75) Inventors: Naoki Taka, Gotenba (JP); Hiroharu Matsuoka, Gotenba (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 349 days.

(21) Appl. No.: 10/510,817

(22) PCT Filed: Apr. 22, 2003

(86) PCT No.: PCT/JP03/05116

§ 371 (c)(1), (2), (4) Date: Oct. 12, 2004

(87) PCT Pub. No.: WO03/091234

PCT Pub. Date: Nov. 6, 2003

(65) Prior Publication Data

US 2005/0124693 A1     Jun. 9, 2005

(30) Foreign Application Priority Data

Apr. 26, 2002 (JP) ............................. 2002-126878

(51) Int. Cl.
*A61K 31/341* (2006.01)
*C07D 307/68* (2006.01)
(52) U.S. Cl. ..................................... 514/471; 549/492
(58) Field of Classification Search ............... 549/492; 514/471
See application file for complete search history.

(56) References Cited

U.S. PATENT DOCUMENTS 2,961,377 A     11/1960     Shapiro et al.

FOREIGN PATENT DOCUMENTS

JP     54-12371     1/1979

OTHER PUBLICATIONS

Shapiro, Seymour L., et al., Hypoglycemic Agents. III., J. Am. Chem. Soc., vol. 81, pp. 3728-3736 (1959).
Drugs in Japan: Ethical Drugs, 23rd Ed., p. 2094, 2000, Japan Pharmaceutical Information Center.

*Primary Examiner*—Bernard Dentz
(74) *Attorney, Agent, or Firm*—Morgan, Lewis & Bockius LLP

(57) ABSTRACT

Diabetes treatments comprising, as effective ingredients, biguanide derivatives represented by the following general formula (1), or salts thereof.

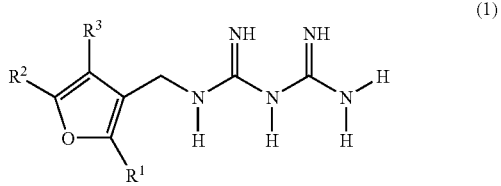

(wherein $R^1$, $R^2$ and $R^3$ may be the same or different and each represents one selected from the group consisting of hydrogen, optionally substituted lower alkyl groups and optionally substituted lower alkylthio groups).

6 Claims, No Drawings

BIGUANIDE DERIVATIVE AND THERAPEUTIC AGENT FOR DIABETES CONTAINING THE SAME

TECHNICAL FIELD

The present invention relates to biguanide derivatives and salts thereof, and to therapeutic agents for the treatment of diabetes comprising the same.

BACKGROUND ART

Treatments for type II (non-insulin dependent) diabetes are currently centered on hypoglycemic agents. Strict blood glucose control clearly lowers rates of transition to complications and mortality rates. The major hypoglycemic agents used are insulin preparations or oral hypoglycemic agents such as sulfonylurea agents, thiazolidine derivatives, α-glucosidase inhibitors, biguanide agents and the like. Among such oral hypoglycemic agents, biguanide agents are known to be the most effective in type II diabetic patients. Numerous biguanide derivatives have been synthesized to date, and the hypoglycemic actions of various biguanide derivatives have been reported in publications such as, for example, J. Am. Chem. Soc., 81, 3728-3736 (1959). However, such biguanide derivatives are commonly recognized as having the potential to induce lactic acidosis, and even the aforementioned publications have not confirmed the presence or degree of blood lactic acid level augmenting effects of biguanide derivatives. Consequently, the existing biguanide agents, such as metformin, have been contraindicated for diabetic patients with anamnesis of lactic acidosis, diabetic patients with kidney dysfunction, diabetic patients with liver dysfunction, diabetic patients with cardiovascular dysfunction, diabetic patients with pulmonary dysfunction, diabetic patients susceptible to hypoxia, diabetic patients consuming excessive alcohol, diabetic patients with gastrointestinal disturbance and elderly diabetic patients, due to the risk of their causing lactic acidosis (DRUGS in JAPAN : Ethical Drugs, 23rd edition, p.2094, 2000, Japan Pharmaceutical Information Center).

In addition, approximately 10% of type II diabetic patients are said to have overt nephropathy, therefore many patients cannot take biguanide agents. Sulfonylurea agents, thiazolidine derivatives and insulin preparations are administered in such cases, but because these agents produce a hunger craving and thus tend to result in increased body weight, such agents cannot be considered suitable for obese diabetic patients. A demand therefore exists for biguanide agents which lower blood glucose substantially without increasing blood lactic acid levels, in order to reduce the risk of inducing lactic acidosis.

DISCLOSURE OF THE INVENTION

The present invention has been accomplished in light of the aforementioned problems of the prior art, and its object is to provide a diabetes treatment which adequately suppresses elevation in blood glucose levels and even satisfactorily lowers blood glucose levels while, preferably, also exhibiting an effect of sufficiently suppressing elevation in blood lactic acid levels, and which can therefore be administered to diabetic patients with kidney dysfunction who are susceptible to lactic acidosis.

As a result of much diligent research directed toward achieving the object, the present inventors found that novel biguanide derivatives having a specific structure exhibit an excellent hypoglycemic effect, and the present invention was completed based on this finding.

Specifically, the present invention provides a biguanide derivative represented by the following general formula (1) or a salt thereof:

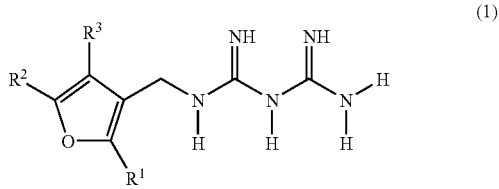

(wherein $R^1$, $R^2$ and $R^3$ may be the same or different and each represents one selected from the group consisting of hydrogen, an optionally substituted lower alkyl group and an optionally substituted lower alkylthio group).

The invention also provides a therapeutic agent for the treatment of diabetes, comprising as an active ingredient, the biguanide derivative represented by general formula (1) above or the salt thereof.

The therapeutic agent for the treatment of diabetes of the invention have excellent hypoglycemic effects (preferably effects of lowering blood glucose without substantial increase of blood lactic acid levels), and is therefore useful as a therapeutic agent for the treatment of diabetes for blood glucose elevation-suppressing therapy which do not induce lactic acidosis. More specifically, it is useful as a therapeutic agent for the treatment of diabetes, wherein the target disease is at least one disease selected from the group consisting of diabetes with anamnesis of lactic acidosis, diabetes with kidney dysfunction, diabetes with liver dysfunction, diabetes with cardiovascular dysfunction, diabetes with pulmonary dysfunction, hypoxia-susceptible diabetes, diabetes with excessive alcohol consumption, diabetes with gastrointestinal disturbance and elderly diabetes, and particularly it is useful as a therapeutic agent for the treatment of diabetes targeted to diabetes with kidney dysfunction.

BEST MODE FOR CARRYING OUT THE INVENTION

Preferred embodiments for carrying out the invention will now be explained in detail. First, the biguanide derivatives of the invention and their salts will be explained.

The biguanide derivatives of the invention are compounds represented by the following general formula (1):

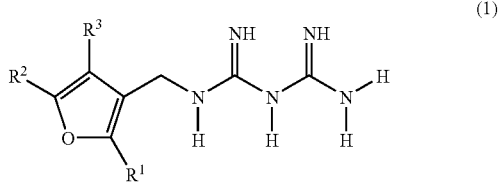

wherein $R^1$, $R^2$ and $R^3$ may be the same or different and each represents one selected from the group consisting of hydrogen, an optionally substituted lower alkyl group and an optionally substituted lower alkylthio group.

As the lower alkyl groups there are preferred linear or branched alkyl groups of 1-6 carbons, and specifically there may be mentioned methyl, ethyl, n-propyl, isopropyl, n-butyl, isobutyl, sec-butyl, tert-butyl, pentyl groups, hexyl groups and the like. Among these lower alkyl groups, those with 1-5 carbons are preferred, those with 1-4 carbons are more preferred, and methyl is especially preferred.

As the lower alkylthio groups there are preferred linear or branched alkylthio groups of 1-6 carbons, and specifically there may be mentioned methylthio, ethylthio, n-propylthio, isopropylthio, n-butylthio, isobutylthio, sec-butylthio, tert-butylthio, pentylthio groups, hexylthio groups and the like. Among these lower alkylthio groups, those with 1-5 carbons are preferred, those with 1-4 carbons are more preferred, and methylthio is especially preferred.

As substituents for the lower alkyl groups and alkylthio groups there may be mentioned lower alkylthio groups and lower alkoxy groups, among which linear or branched alkylthio groups of 1-6 (more preferably 1-4) carbons are preferred, and methylthio is especially preferred.

As the novel biguanide derivatives according to the invention there may be mentioned, specifically, 1-[(furan-3-yl)methyl]biguanide, 1-[(2-methylfuran-3-yl)methyl]biguanide, 1-[(4-methylfuran-3-yl)methyl]biguanide, 1-[(5-methylfuran-3-yl)methyl]biguanide, 1-[(2-ethylfuran-3-yl)methyl]biguanide, 1-[(4-ethylfuran-3-yl)methylgbiguanide, 1-[(5-ethylfuran-3-yl)methyl]biguanide, 1-[(2-tert-butylfuran-3-yl)methyl]biguanide, 1-[(4-tert-butylfuran-3-yl)methyl]biguanide, 1-[(5-tert-butylfuran-3-yl)methyl]biguanide, 1-[(2,4-dimethylfuran-3-yl)methyl]biguanide, 1-[(2,5-dimethylfuran-3-yl)methyl]biguanide, 1-[(4,5-dimethylfuran-3-yl)methyl]biguanide, 1-[(2,4,5-trimethylfuran-3-yl)methyl] biguanide, 1-[(2-methylthiomethylfuran-3-yl)methyl] biguanide, 1-[(4-methylthiomethylfuran-3-yl)methyl] biguanide, 1-[(5-methylthiomethylfuran-3-yl)methyl] biguanide, and the like.

The salts of biguanide derivatives represented by general formula (1) above may be in the form of pharmacologically acceptable salts, such as, for example, inorganic acid salts, organic acid salts, acidic amino acid salts and the like. As examples of inorganic acid salts there may be mentioned salts with hydrochloric acid, hydrobromic acid, nitric acid, sulfuric acid and phosphoric acid. As examples of organic acid salts there may be mentioned salts with formic acid, acetic acid, trifluoroacetic acid, fumaric acid, oxalic acid, tartaric acid, maleic acid, citric acid, succinic acid, malic acid, methanesulfonic acid, benzenesulfonic acid and p-toluenesulfonic acid. As examples of acidic amino acid salts there may be mentioned salts with aspartic acid and glutamic acid. Preferred among these salts of biguanide derivatives represented by general formula (1) are salts with inorganic acids, and especially salts with hydrochloric acid.

The compounds represented by general formula (1) may be synthesized using the corresponding (furan-3-yl)methylamine or (substituted furan-3-yl)methylamine as starting materials. Commercially available (furan-3-yl)methylamine (manufactured by Maybridge Chemical, for example) may be used. As a (substituted furan-3-yl)methylamine there may be used one produced by the following reaction scheme. In this reaction scheme, $R^1$, $R^2$ and $R^3$ have the same definitions as $R^1$, $R^2$ and $R^3$ in general formula (1) above.

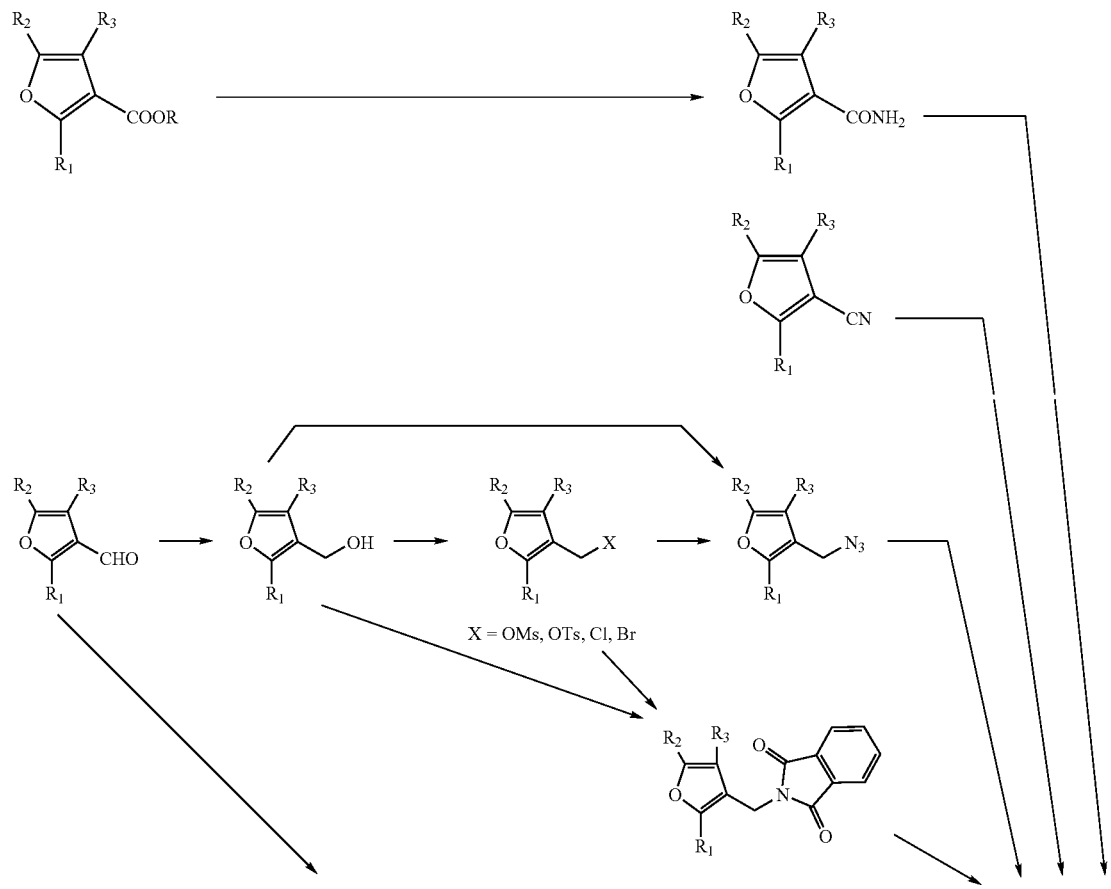

-continued

A target (substituted furan-3-yl)methylamine may be obtained by reducing the corresponding substituted furan-3-carboxamide (J. Med. Chem., 42(15), 2920-2926(1999)), substituted furan-3-carbonitrile (J. Heterocycl. Chem., 33(6), 2007-2011(1996)), (substituted furan-3-yl)methylazide or substituted furan-3-carbaldehyde oxime. Alternatively, it may be synthesized from a (substituted furan-3-yl)methylphthalimide (J. Med. Chem., 42(5), 2920-2926(1999)). A substituted furan-3-carboxamide may be synthesized from the corresponding substituted furan-3-carboxylic acid ester. A (substituted furan-3-yl)methylazide and (substituted furan-3-yl)methylphthalimide may be directly synthesized from a (substituted furan-3-yl)methyl alcohol by Mitsunobu reaction, or they may be synthesized via an alkylsulfonate such-as mesyl or tosyl, or a halogenated compound such as chloro or bromo. A (substituted furan-3-yl)methyl alcohol may be synthesized by reduction of the corresponding substituted furan-3-carbaldehyde. A substituted furan-3-carbaldehyde oxime may be obtained by reaction of the corresponding substituted furan-3-carbaldehyde and hydroxylamine.

Cyanoguanidine may be mentioned as an additional starting material to be used for production of a compound represented by general formula (1), and it may be commercially available products (for example, by Tokyo Kasei, Kanto Chemicals, Wako Pure Chemical Industries or Aldrich).

The compounds represented by general formula (1) may be produced by reaction with cyanoguanidine in the presence of silylating agents, either in solvents that do not affect the (furan-3-yl)methylamine or (substituted furan-3-yl)methylamine reaction, or without solvents. As examples of such solvents there may be mentioned hexane, cyclohexane, benzene, toluene, diethyl ether, diisopropyl ether, tert-butylmethyl ether, tetrahydrofuran, dioxane, dichloromethane, 1,2-dichloroethane and chloroform, with dichloromethane, 1,2-dichloroethane, benzene and toluene being preferred. These solvents may also be used in mixed solvents of two or more.

The reaction temperature is not particularly restricted so long as it is a temperature from −78° C. to the boiling point of the reaction mixture, but it is preferably room temperature.

As examples of silylating agents there may be mentioned chlorotrimethylsilane ($Me_3SiCl$ ($Me_3Si$ will hereinafter be abbreviated as TMS)), chlorotriethylsilane ($Et_3SiCl$), trimethylsilyl trifluoromethanesulfonate ($TMSOSO_2CF_3$), trimethylsilyl methanesulfonate ($TMSOSO_2CH_3$), $(TMSO)_2SO_2$, $t\text{-}BuMe_2SiOSO_2CF_3$, (TMSO)(TMSN)CMe, among which trimethylsilyl trifluoromethanesulfonate and trimethylsilyl methanesulfonate are preferred.

A scheme for the production method for the compounds represented by general formula (1) is shown below. The symbols $R^1$, $R^2$ and $R^3$ in the scheme have the same definition as $R^1$, $R^2$ and $R^3$ in general formula (1) above.

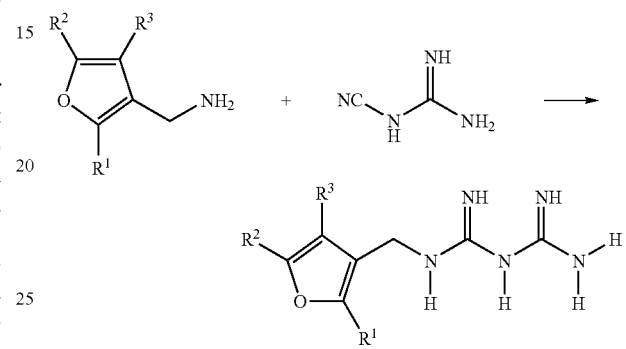

Next, the therapeutic agent for the treatment of diabetes of the invention will be explained. The therapeutic agent for the treatment of diabetes of the invention comprises as an active ingredient the biguanide derivative represented by the general formula (1) or the salt thereof. There are no particular restrictions on the specific formulations of the therapeutic agent for the treatment of diabetes of the invention, so long as it comprises the above-mentioned biguanide derivatives or the salts thereof as an active ingredient, and for example, they may be in admixture with additives such as excipients, binders, stabilizers, lubricants, taste correctors, disintegrants, coating agents, coloring agents, buffering agents, aqueous solvents, oily solvents, isotonizing agents, dispersing agents, preservatives, solubilizing agents, fluidizing agents, soothing agents, pH adjustors, antiseptics, bases and the like. Physiologically acceptable carriers may also be used as additives in the therapeutic agent for the treatment of diabetes.

As examples of excipients there may be mentioned sugars such as lactose, saccharose, glucose, D-mannitol and sorbit, cellulose and its derivatives such as crystalline cellulose, hydroxypropyl cellulose, hydroxypropylmethyl cellulose and methyl cellulose, starches and their derivatives such as corn starch, potato starch, α-starch, dextrin, β-cyclodextrin, carboxymethyl starch sodium and hydroxypropyl starch, silicates such as synthetic aluminum silicate, magnesium aluminosilicate, calcium silicate and magnesium silicate, phosphates such as calcium phosphate, carbonates such as calcium carbonate, sulfates such as calcium sulfate, and tartaric acid, potassium hydrogen tartrate, magnesium hydroxide and the like.

As examples of binders there may be mentioned cellulose and its derivatives such as crystalline cellulose, hydroxypropyl cellulose, hydroxypropylmethyl cellulose and methyl cellulose, starches and their derivatives such as corn starch, potato starch, α-starch, dextrin, β-cyclodextrin, carboxymethyl starch sodium and hydroxypropyl starch, sugars such as lactose, saccharose, glucose, D-mannitol and sorbit, and agar, stearyl alcohol, gelatin, tragacanth, polyvinyl alcohol, polyvinyl pyrrolidone, and the like.

As examples of stabilizers there may be mentioned parahydroxybenzoic acid esters such as methyl paraben and propyl paraben, alcohols such as chlorobutanol, benzyl alcohol and phenylethyl alcohol, phenols such as phenol and cresol, sulfite salts such as sodium bisulfite and sodium sulfite, edetic acid salts such as sodium edetate and tetrasodium edetate, and hydrogenated oils, sesame oil, sodium chondroitin sulfate, dibutylhydroxytoluene, adipic acid, ascorbic acid, stearic L-ascorbate esters, sodium L-ascorbate, L-aspartic acid, sodium L-aspartate, acetyltryptophan sodium, acetanilide, aprotinin solution, aminoethylsulfonic acid, aminoacetic acid, DL-alanine, L-alanine, benzalkonium chloride, sorbic acid and the like.

As examples of lubricants there may be mentioned stearic acids such as stearic acid, calcium stearate and magnesium stearate, waxes such as white beeswax and carnauba wax, sulfates such as sodium sulfate, silicic acid compounds such as magnesium silicate and light silicic anhydride, lauryl sulfates such as sodium lauryl sulfate, and gum arabic powder, cacao butter, carmellose calcium, carmellose sodium, callopeptide, hydrated silicon dioxide, hydrated amorphous silicon oxide, dry aluminum hydroxide gel, glycerin, light liquid paraffin, crystalline cellulose, hydrogenated oil, synthetic aluminum silicate, sesame oil, wheat starch, talc, macrogols, phosphoric acid and the like.

As examples of taste correctors there may be mentioned sugars such as lactose, saccharose, glucose and D-mannitol, and ascorbic acid, L-aspartic acid, sodium L-aspartate, magnesium L-aspartate, aspartame, sweet hydrangea, sweet hydrangea extract, sweet hydrangea powder, aminoethylsulfonic acid, aminoacetic acid, DL-alanine, saccharin sodium, dl-menthol, 1-menthol and the like.

As examples of disintegrants there may be mentioned cellulose and its derivatives such as crystalline cellulose, hydroxypropyl cellulose, hydroxypropylmethyl cellulose and methyl cellulose, carbonates such as calcium carbonate, sodium bicarbonate and magnesium carbonate, starches and their derivatives such as corn starch, potato starch, α-starch, dextrin, β-cyclodextrin, carboxymethyl starch sodium and hydroxypropyl starch, and gelatin, tragacanth, adipic acid, alginic acid, sodium alginate and the like.

As examples of coating agents there may be mentioned cellulose derivatives such as cellulose acetate, hydroxypropyl cellulose, cellulose acetate phthalate and hydroxypropylmethyl cellulose, and shellac, polyvinyl pyrrolidones, polyethylene glycol, macrogols, methacrylic acid copolymers, liquid paraffin, eudragit, and the like.

As examples of coloring agents there may be mentioned indigo carmine, caramel, riboflavin and the like.

As examples of buffering agents there may be mentioned aminoacetic acid, L-arginine, benzoic acid, sodium benzoate, ammonium chloride, potassium chloride, sodium chloride, dried sodium sulfite, dried sodium carbonate, diluted hydrochloric acid, citric acid, calcium citrate, sodium citrate, disodium citrate, calcium gluconate, L-glutamic acid, sodium L-glutamate, creatihine, chlorobutanol, crystalline sodium dihydrogen phosphate, disodium succinate, acetic acid, potassium acetate, sodium acetate, tartaric acid, sodium bicarbonate, sodium carbonate, triethanolamine, lactic acid, sodium lactate solution, glacial acetic acid, boric acid, maleic acid, citric anhydride, anhydrous sodium citrate, anhydrous sodium acetate, anhydrous sodium carbonate, anhydrous sodium hydrogen phosphate, anhydrous trisodium phosphate, anhydrous sodium dihydrogen phosphate, dl-malic acid, phosphoric acid, trisodium phosphate, sodium hydrogen phosphate, dipotassium phosphate, potassium dihydrogen phosphate, sodium dihydrogen phosphate, sodium dihydrogen phosphate hydrate and the like.

As examples of aqueous solvents there may be mentioned distilled water, physiological saline, Ringer's solution and the like.

As examples of oily solvents there may be mentioned vegetable oils such as olive oil, sesame oil, cotton oil and corn oil, and propylene glycol, and the like.

As examples of isotonizing agents there may be mentioned potassium chloride, sodium chloride, glycerin, sodium bromide, D-sorbitol, nicotinamide, glucose, boric acid and the like.

As examples of dispersing agents there may be mentioned stearic acid and its salts such as zinc stearate and magnesium stearate, and gum arabic, propyleneglycol alginate, sorbitan sesquioleate, D-sorbitol, tragacanth, methyl cellulose, aluminum monostearate, aminoalkyl methacrylate copolymer RS, lactose, concentrated glycerin, propylene glycol, macrogols, sodium lauryl sulfate and the like.

As examples of preservatives there may be mentioned alcohols such as chlorobutanol, phenethyl alcohol, propylene glycol and benzyl alcohol, parahydroxybenzoic acid esters such as isobutyl parahydroxybenzoate, ethyl parahydroxybenzoate and methyl parahydroxybenzoate, and benzalkonium chloride, benzethonium chloride, dried sodium sulfite, dried sodium sulfate, cresol, chlorocresol, dibutylhydroxytoluene, potassium sorbate, sodium dehydroacetate, phenol, formalin, phosphoric acid, benzoin, thimerosal, thymol, sodium dehydroacetate and the like.

As examples of solubilizing agents there may be mentioned sodium benzoate, ethylenediamine, citric acid, sodium citrate, glycerin, sodium acetate, sodium salicylate, sorbitan sesquioleate, nicotinamide, glucose, benzyl alcohol, polyvinyl pyrrolidones, acetone, ethanol, isopropanol, D-sorbitol, sodium hydrogen carbonate, sodium carbonate, lactose, urea, saccharose and the like.

As examples of fluidizing agents there may be mentioned stearic acid and its salts such as calcium stearate and magnesium stearate, and hydrated silicon dioxide, talc, absolute ethanol, crystalline cellulose, synthetic aluminum silicate, calcium hydrogen phosphate and the like.

As examples of soothing agents there may be mentioned benzalkonium chloride, procaine hydrochloride, meprylcaine hydrochloride, lidocaine hydrochloride, lidocaine and the like.

As examples of pH adjustors there may be mentioned hydrochloric acid, citric acid, succinic acid, acetic acid, boric acid, maleic acid, sodium hydroxide and the like.

As examples of antiseptics there may be mentioned benzoic acid, sodium benzoate, cetylpyridinium chloride, salicylic acid, sodium salicylate, sorbic acid, potassium sorbate, thymol, methyl parahydroxybenzoate, butyl parahydroxybenzoate and the like.

As examples of bases there may be mentioned vegetable oils such as olive oil, sesame oil and wheat germ oil, and glycerin, stearyl alcohol, polyethylene glycols, propylene glycol, cetanol, lard, white vaseline, paraffin, bentonite, isopropyl lanolin fatty acids, vaseline, polysorbates, macrogols, lauryl alcohol, sodium lauryl sulfate, ethyl linoleate, sodium hydrogen phosphate, rosins and the like.

The amount of the biguanide derivative represented by general formula (1) or the salt thereof in the therapeutic agent for the treatment of diabetes of the invention will differ depending on the dosage form, but is preferably from 0.00001-100 wt % with respect to the total of the therapeutic agent for the treatment of diabetes (pharmaceutical composition).

There are no particular restrictions on the dosage form of the therapeutic agent for the treatment of diabetes according to the invention, and as examples of oral forms there may be mentioned granules, powders, tablets, capsules, syrups, emulsions, suspensions and the like, while as examples of parenteral forms there may be mentioned injections such as subcutaneous injections, intravenous injections, intramuscular injections and intraperitoneal injections, percutaneous administration forms such as ointments, creams and lotions, suppository forms such as rectal suppositories and vaginal suppositories, and intranasal administration forms and the like.

The process for producing the therapeutic agent for the treatment of diabetes according to the invention employs a biguanide derivative represented by general formula (1) above or a salt thereof, to produce the therapeutic agent for the treatment of diabetes (preferably a therapeutic agent for the treatment of diabetes with an effect of lowering blood glucose without substantial increase of blood lactic acid levels, or therapeutic agent for the treatment of diabetes for blood glucose elevation-suppressing therapy which does not induce lactic acidosis). There are no particular restrictions on the specific process used, and the formulations comprising a biguanide derivative represented by general formula (1) or a salt thereof may be produced by publicly known processes which are commonly used in drug formulation steps. Specifically, such formulations may be obtained by appropriate mixture of prescribed amounts of the biguanide derivative represented by general formula (1) or the salt thereof, with the additive components, as suitable for the dosage form of the desired therapeutic agent for the treatment of diabetes.

The effect of "lowering blood glucose levels without substantial increase of blood lactic acid levels", as the preferred effect of the therapeutic agent for the treatment of diabetes according to the invention, will now be explained.

In the invention, lowering blood glucose levels without substantial increase of blood lactic acid levels means that when blood glucose reduction rate and blood lactic acid levels are measured by an oral glucose tolerance test, the dosage of the therapeutic agent for the treatment of diabetes which exhibits a blood glucose reduction rate of 60-80% results in a blood lactic acid level increase rate of preferably no greater than 35%, more preferably 30%, particularly preferably 25%. For example, when blood glucose reduction rate and blood lactic acid levels are measured by the aforementioned oral glucose tolerance test for a typical diabetes patient exhibiting an initial blood lactic acid level of 4-33 mg/dL, preferably even administration of the therapeutic agent for the treatment of diabetes at a dose which exhibits a blood glucose reduction rate of 60-80% does not increase the blood lactic acid level above 45 mg/dL. Also, at a dose of the therapeutic agent for the treatment of diabetes which exhibits a blood glucose reduction rate of 40-60%, the blood lactic acid level increase rate is preferably no greater than 15%, more preferably 10%. For example, when blood glucose reduction rate and blood lactic acid levels are measured by the aforementioned oral glucose tolerance test for a typical diabetes patient exhibiting an initial blood lactic acid level of 4-33 mg/dL, preferably even administration of the therapeutic agent, for the treatment of diabetes at a dose which exhibits a blood glucose reduction rate of 40-60% does not increase the blood lactic acid level above 38 mg/dL.

Measurement of blood glucose reduction rate and blood lactic acid levels by the aforementioned oral glucose tolerance test may be carried out by a publicly known method, and preferred methods are described below. Specifically, 11- to 17-week-old female mice (C57BLKS/J-m +/+ Lepr<db> (db/db)) are starved for 18-24 hours. A group of five or six mice is used for the test. Blood is sampled from the tail for measurement of the blood glucose levels and blood lactic acid levels before treatment as controls. After sampling, the biguanide derivative is dissolved in phosphate-buffered physiological saline at a suitable concentration and subcutaneously administered at a dose of 5 ml/kg. As controls are prepared mice administered only the solvent. Glucose is then administered orally at a dose of 3 g/6 ml/kg at 30 minutes after administration of the compound or solvent as an oral glucose tolerance test. Blood is sampled from the tail for measurement of the blood glucose levels and the blood lactic acid levels 30 minutes, 1 hour and 2 hours after glucose administration. The blood glucose levels are measured using a New Blood Sugar Test (Roche Diagnostics) or a Glucose CII-Test Wako (Wako Pure Chemical Industries, Ltd.). The blood lactic acid levels are measured using an "Asuka Sigma" (Sigma Diagnostics).

The blood glucose reduction rate and the blood lactic acid level increase rate are calculated according to the following formulas.

Blood glucose reduction rate (%)=[($AUC$ for blood glucose increase level of solvent-administered group–$AUC$ for blood glucose increase level of compound-administered group)/$AUC$ for blood glucose increase level of solvent-administered group]×100

The AUC for blood glucose increase level represents the area of the increase portion in a graph of the blood glucose level changes after glucose administration plotted with respect to time, up to 2 hours after glucose administration, with the glucose level prior to glucose administration as the baseline. Specifically, the AUC for the blood glucose increase level may be calculated by the following formula, where A=blood glucose level before glucose administration, B=blood glucose level 30 minutes after glucose administration, C=blood glucose level 1 hour after glucose administration, D=blood glucose level 2 hours after glucose administration.

$AUC$ for blood glucose increase level=$0.5\times((A+B)/2-A)+0.5\times((B+C)/2-A)+1\times((C+D)/2-A)$ The blood lactic acid level increase rate is calculated according to the following formula.

Blood lactic acid level increase rate (%)=[($AUC$ for blood lactic acid level of compound-administered group–$AUC$ for blood lactic acid level of solvent-administered group)/$AUC$ for blood lactic acid level of solvent-administered group]×100

The AUC for blood lactic acid level represents the area in a graph of the blood lactic acid level changes after glucose administration plotted with respect to time, up to 2 hours after glucose administration. Specifically, the AUC for the blood lactic acid level may be calculated by the following formula, where E=blood lactic acid level before glucose administration, F=blood lactic acid level 30 minutes after glucose administration, G=blood lactic acid level 1 hour after glucose administration, H=blood lactic acid level 2 hours after glucose administration.

$AUC$ for blood lactic acid level=$0.5\times(E+F)/2+0.5\times(F+G)/2+1\times(G+H)/2$ The preferred object of administration will be explained.

The therapeutic agent for the treatment of diabetes according to the invention have the excellent hypoglycemic effect as described above, and it preferably lower blood glucose levels without substantial increase of blood lactic acid levels. It is therefore useful for treatment to suppress blood glucose level increase which do not induce lactic acidosis, and are effective for administration to diabetic patients and especially to diabetic patients who are prone to lactic acidosis. Diabetic patients prone to lactic acidosis include, for example, diabetic patients with lactic acidosis anamnesis, diabetic patients with kidney dysfunction, diabetic patients with liver dysfunction, diabetic patients with cardiovascular dysfunction, diabetic patients with pulmonary dysfunction, diabetic patients susceptible to hypoxia, diabetic patients consuming excessive alcohol, diabetic patients with gastrointestinal disturbance and elderly diabetic patients.

The therapeutic agent for the treatment of diabetes according to the invention is particularly effective for diabetic patients who are prone to lactic acidosis as explained above, and are especially suitable for administration to diabetic patients with kidney dysfunction. Kidney dysfunction includes, specifically, for example chronic renal failure, diabetic nephropathy, glomerular nephritis, immune complex nephritis, acute renal failure, interstitial nephritis, renal sclerosis, renal infarction, abnormal tubular function, drug-induced nephropathy, agricultural chemical-induced nephropathy, uremia, and the like.

A method of suppressing blood glucose elevation and a method of treating diabetes using the biguanide derivative of the invention or the salt thereof will now be explained. The method of suppressing blood glucose elevation may be a method of administering a biguanide derivative represented by general formula (1) or a salt thereof, and preferably it is a method of suppressing blood glucose elevation without substantial increase of blood lactic acid levels. As a method of treating diabetes there may be mentioned a method comprising a step of administering an effective dose of a biguanide derivative represented by general formula (1) or a salt thereof to at least one type of diabetes patient selected from the group consisting of diabetic patients with anamnesis of lactic acidosis, diabetic patients with kidney dysfunction, diabetic patients with liver dysfunction, diabetic patients with cardiovascular dysfunction, diabetic patients with pulmonary dysfunction, diabetic patients susceptible to hypoxia, diabetic patients consuming excessive alcohol, diabetic patients with gastrointestinal disturbance and elderly diabetic patients, and a step of suppressing blood glucose elevation (preferably a step of suppressing blood glucose elevation without substantial increase of blood lactic acid levels).

The method of administering the therapeutic agent for the treatment of diabetes according to the invention is not particularly restricted, and for example, the agent may be administered orally or parenterally as a pharmaceutical composition (preparation) using the aforementioned additives with a biguanide derivative represented by general formula (1) or its pharmacologically acceptable salt.

The dosage of a biguanide derivative represented by general formula (1) or its salt may be appropriately determined based on the species of subject (human or other warm-blooded animal, for example), the severity of symptoms, the age, route of administration, physician diagnosis, etc., and for an adult, for example, the dosage of a biguanide derivative represented by general formula (1) will be preferably 0.1-2000 mg/kg per day in the case of oral administration, and preferably 0.1-1000 mg/kg per day in the case of parenteral administration. These dosages are the values per unit weight (1 kg) of the subject of administration. According to the invention, the dosage may be administered once during a period of 1-7 days or divided over several times, depending on the severity of symptoms, the physician diagnosis, etc.

By thus administering an effective dose of a biguanide derivative represented by general formula (1) or its salt, it is possible, as described above, to adequately suppress increase in blood glucose levels, and to sufficiently lower blood glucose levels, preferably adequately inhibiting increase in blood lactic acid levels.

EXAMPLES

The present invention will now be explained in greater detail through examples and comparative examples, with the understanding that these examples are not limitative on the invention.

Examples 1-2 and Comparative Examples 1-16

Synthesis Example 1

Synthesis of 1-[(furan-3-yl)methyl]biguanide)

To a solution of (furan-3-yl)methylamine (1.79 g) in 1,2-dichloroethane (13 mL) was added trimethylsilyl trifluoromethanesulfonate (4.00 mL), and the mixture was stirred at room temperature for 30 minutes, and then cyanoguanidine (1.55 g) was added, and the mixture was further stirred at room temperature for 1.5 hours, and heated and stirred for 3 hours in an oil bath at 50° C. The reaction mixture was subjected to amine-treated silica gel column chromatography (methanol:chloroform=10:100) to give the target compound (2.30 g) as an oil. The results of structural analysis of the resultant oil were as follows.

$^1$H-NMR (DMSO-$d_6$) δ: 4.15 (2H, s), 6.47 (1H, brs), 6.40-8.30 (6H, m), 7.59 (2H, brs)

MS (ESI$^+$): 182 [M+1]$^+$

HPLC RT: 6.2 min (mobile phase: 10% methanol)

The structural formula of the obtained compound is shown below.

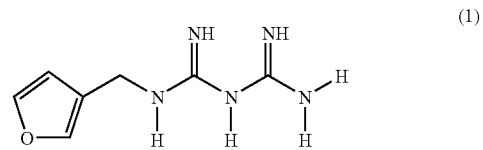

(1)

The amine-treated silica gel chromatography was conducted using a Silica Gel Chromatorex NH DM1020 (10 mm particle size) by Fuji Silysia Chemical Co., Ltd. The HPLC apparatus was L-6200 by Hitachi, the HPLC column was Develosil ODS HG-5, 4.6×150 mm by Nomura Chemical, and measurement of the retention time (RT: min) by HPLC was carried out by the following method. Specifically, an aqueous solution of 10% methanol/0.1 M ammonium acetate was used as the mobile phase, with a flow rate of 1 ml/min and detection at 240 nm. LCMS was conducted by the ionization method (ESI$^+$) using LCQ by Thermo Finigan.

(Oral Glucose Tolerance Test)

Eleven- to seventeen-week-old female mice (C57BLKS/J-m +/+ Lepr<db> (db/db)) were starved for 18-24 hours, and a group of six mice was used for the test. Blood was sampled from the tail for measurement of the blood glucose levels and blood lactic acid levels before treatment. After sampling, the compounds listed in Table 1 (Examples 1-2) were dissolved in phosphate-buffered physiological saline to give the dosages also listed in Table 1, and were subcutaneously administered to the mice at a dose of 5 ml/kg. For comparison, phenformin in the doses shown in Table 1 (Comparative Examples 1-8) and metformin in the doses shown in Table 1

(Comparative Examples 9-16) was subcutaneously administered to mice similarly. As a control, the solvent alone was subcutaneously administered to mice similarly.

Glucose was then administered orally at a dose of 3 g/6 ml/kg at 30 minutes after administration of the compound or solvent as an oral glucose tolerance test. Blood was sampled from the tail for measurement of the blood glucose levels and blood lactic acid levels 30 minutes, 1 hour and 2 hours after glucose administration. The blood glucose levels were measured using a New Blood Sugar Test (Roche Diagnostics) or a Glucose CII-Test Wako (Wako Pure Chemical Industries, Ltd.). The blood lactic acid levels were measured using an "Asuka Sigma" (Sigma Diagnostics).

The test results (blood glucose reduction rates and blood lactic acid level increase rates) are shown in Table 1.

TABLE 1

| | Compound | Dosage (mg/kg) | Blood glucose reduction rate (%) | Blood lactic acid level increase rate (%) |
|---|---|---|---|---|
| Ex.1 | 1-[(Furan-3-yl)methyl]biguanide | 50 | 40.3 | — |
| Ex. 2 | 1-[(Furan-3-yl)methyl]biguanide | 75 | 65.5 | 9.7 |
| Comp. Ex. 1 | Phenformin | 37.5 | 39.5 | 46.4 |
| Comp. Ex. 2 | Phenformin | 37.5 | 72.7 | 83.1 |
| Comp. Ex. 3 | Phenformin | 75 | 64.5 | 93.6 |
| Comp. Ex. 4 | Phenformin | 75 | 78.0 | 151.6 |
| Comp. Ex. 5 | Phenformin | 75 | 60.8 | 94.7 |
| Comp. Ex. 6 | Phenformin | 75 | 61.4 | 120.8 |
| Comp. Ex. 7 | Phenformin | 75 | 72.8 | 141.1 |
| Comp. Ex. 8 | Phenformin | 75 | 69.6 | 114.8 |
| Comp. Ex. 9 | Metformin | 100 | 29.1 | 4.1 |
| Comp. Ex. 10 | Metformin | 100 | 12.9 | 3.7 |
| Comp. Ex. 11 | Metformin | 150 | 32.5 | 25.8 |
| Comp. Ex. 12 | Metformin | 150 | 24.0 | 10.7 |
| Comp. Ex. 13 | Metformin | 150 | 19.6 | 20.2 |
| Comp. Ex. 14 | Metformin | 150 | 48.3 | 16.5 |
| Comp. Ex. 15 | Metformin | 200 | 56.0 | 36.0 |
| Comp. Ex. 16 | Metformin | 200 | 41.8 | 61.5 |

Consequently, administration of a biguanide derivative of the invention represented by general formula (1) above or its salt was confirmed to extremely minimize increase in blood lactic acid levels while exhibiting a notable hypoglycemic effect.

INDUSTRIAL APPLICABILITY

As explained above, the biguanide derivative of the invention and the salt thereof can be used to provide a therapeutic agent for the treatment of diabetes which adequately suppress blood glucose level elevation and even adequately lower blood glucose levels, and preferably do so while adequately inhibiting blood lactic acid level elevation. The invention can therefore satisfactorily suppress blood glucose level elevation while avoiding blood lactic acid level increase, and thereby provides an agent for prevention or treatment of hyperglycemia that also prevent lactic acid acidosis, for diabetic patients who are susceptible to lactic acidosis.

The invention claimed is:

1. A biguanide derivative represented by the following general formula (1) or a salt thereof:

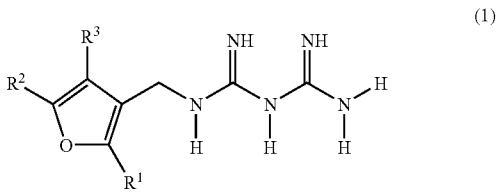

(1)

(wherein $R^1$, $R^2$ and $R^3$ may be the same or different and each represents one selected from the group consisting of hydrogen, an optionally substituted lower alkyl group and an optionally substituted lower alkylthio group).

2. A therapeutic agent for the treatment of diabetes, comprising as an active ingredient a biguanide derivative represented by the following general formula (1) or a salt thereof:

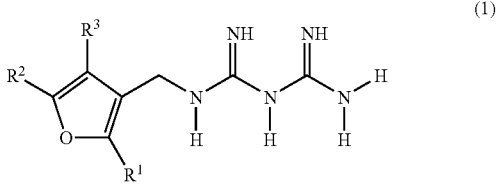

(1)

(wherein $R^1$, $R^2$ and $R^3$ may be the same or different and each represents one selected from the group consisting of hydrogen, an optionally substituted lower alkyl group and an optionally substituted lower alkylthio group).

3. The therapeutic agent for the treatment of diabetes according to claim 2, which has an effect of lowering blood glucose levels without a substantial increase of blood lactic acid levels.

4. The therapeutic agent for the treatment of diabetes according to claim 2 or 3, wherein the target disease is at least one disease selected from the group consisting of diabetes with anamnesis of lactic acidosis, diabetes with kidney dysfunction, diabetes with liver dysfunction, diabetes with cardiovascular dysfunction, diabetes with pulmonary dysfunction, hypoxia-susceptible diabetes, diabetes with excessive alcohol consumption, diabetes with gastrointestinal disturbance and elderly diabetes.

5. The therapeutic agent for the treatment of diabetes according to claim 4, wherein the target disease is diabetes with kidney dysfunction.

6. The therapeutic agent for the treatment of diabetes according to claim 2, which is used for the suppression of blood glucose elevation without inducing lactic acidosis.

* * * * *